(12) United States Patent
Petersen (10) Patent No.: US 7,647,704 B2
(45) Date of Patent: Jan. 19, 2010

(54) HANDLE WITH REMOVABLE DISPOSABLE SURGICAL BLADE

(76) Inventor: Thomas D. Petersen, 9680 Alto Dr., La Mesa, CA (US) 91941

( * ) Notice: Subject to any disclaimer, the term of this patent is extended or adjusted under 35 U.S.C. 154(b) by 697 days.

(21) Appl. No.: 11/320,716

(22) Filed: Dec. 30, 2005

(65) Prior Publication Data

US 2007/0156160 A1 Jul. 5, 2007

(51) Int. Cl.
A61B 17/32 (2006.01)
B25G 1/00 (2006.01)
B25G 3/00 (2006.01)

(52) U.S. Cl. ............ 30/329; 30/337; 30/339; 30/340; 30/342; 606/167

(58) Field of Classification Search ........... 30/329–339, 30/340, 342; 606/167; D24/147
See application file for complete search history.

(56) References Cited

U.S. PATENT DOCUMENTS

| | | | | |
|---|---|---|---|---|
| 1,226,636 A * | 5/1917 | Brown | .......... | 30/337 |
| 1,261,815 A * | 4/1918 | Housdorfer | .......... | 30/333 |
| 1,577,880 A * | 3/1926 | Stuart | .......... | 30/340 |
| 1,608,781 A * | 11/1926 | Efantis | .......... | 30/337 |
| 1,625,778 A * | 4/1927 | Nickerson | .......... | 30/337 |
| 1,651,856 A * | 12/1927 | Weiss | .......... | 30/337 |
| 1,813,723 A * | 7/1931 | Beaver | .......... | 30/329 |
| 1,813,782 A * | 7/1931 | Thompson | .......... | 30/338 |
| 1,888,488 A * | 11/1932 | Brown | .......... | 30/337 |
| 1,888,489 A * | 11/1932 | Brown | .......... | 30/333 |

(Continued)

FOREIGN PATENT DOCUMENTS

EP 769276 A1 * 4/1997

(Continued)

*Primary Examiner*—Jason Daniel Prone
(74) *Attorney, Agent, or Firm*—H. Jay Spiegel (57) ABSTRACT

A surgical blade includes a handle with a recess sized to receive the proximal end of a blade assembly. The recess includes a notch as well as opposed facing distal ridges designed to engage elevated surfaces in the blade assembly to maintain the blade assembly and handle assembled. The blade assembly includes a blade portion and a fitting having a protrusion sized to be received in the proximal notch of the recess in the handle when the blade portion is assembled to the handle. The fitting also includes side faces having opposed elevated surfaces obliquely disposed so that they are engaged by the distal ridges within the handle recess. The fitting also includes an upwardly extending catch that engages a distal surface on the handle to assist in locking the blade assembly to the handle. The recess of the handle includes inner tapered surfaces. The side faces of the fitting are tapered to the same degree so that as the fitting is pushed upwardly within the recess, the side faces of the fitting engage the lateral inner surfaces of the recess to provide an interference fit therebetween. A blade removal system permits the blade assembly to be removed from the handle without any danger of cutting or puncturing the fingers or hands of the surgeon. The system includes a container having a removable lid, with the lid having an opening leading to a short passageway receiving the blade assembly. The blade assembly may be inserted into the recess until the fitting engages within a rectangular opening therein. In that orientation, the handle may be pivoted to unlock the blade assembly from the handle.

15 Claims, 10 Drawing Sheets

U.S. PATENT DOCUMENTS

| | | | | |
|---|---|---|---|---|
| 1,915,244 | A | * | 6/1933 | Beaver ................... 30/335 |
| 1,940,855 | A | * | 12/1933 | Friedman ................ 30/339 |
| 2,240,387 | A | * | 4/1941 | Crank et al. ............. 30/337 |
| 2,650,426 | A | * | 9/1953 | Montelius ............... 30/340 |
| 2,960,769 | A | * | 11/1960 | Matwijcow ............. 30/340 |
| 3,109,237 | A | * | 11/1963 | Girouard ................. 30/329 |
| 3,262,205 | A | * | 7/1966 | Arden ..................... D24/147 |
| 3,311,976 | A | * | 4/1967 | Matwijcow ............. 30/340 |
| 3,886,656 | A | * | 6/1975 | Meshulam et al. ...... 30/337 |
| 4,014,343 | A | * | 3/1977 | Esty ........................ 606/45 |
| 5,330,493 | A | * | 7/1994 | Haining ................... 606/167 |
| 5,342,379 | A | * | 8/1994 | Volinsky ................. 606/167 |
| 5,344,424 | A | * | 9/1994 | Roberts et al. .......... 606/167 |
| 5,481,804 | A | * | 1/1996 | Platts ...................... 30/335 |
| 5,556,409 | A | * | 9/1996 | Haining ................... 30/162 |
| 5,571,127 | A | * | 11/1996 | DeCampli ............... 606/167 |
| 5,578,050 | A | * | 11/1996 | Webb ...................... 606/167 |
| 6,105,262 | A | * | 8/2000 | Rickard ................... 30/332 |
| 6,216,868 | B1 | * | 4/2001 | Rastegar et al. ......... 30/329 |
| 6,500,187 | B1 | * | 12/2002 | Petersen .................. 606/167 |
| 6,629,985 | B1 | * | 10/2003 | Kiehne .................... 606/167 |
| 6,948,250 | B1 | * | 9/2005 | Caiafa et al. ............ 30/335 |

FOREIGN PATENT DOCUMENTS

| | | | |
|---|---|---|---|
| EP | 948937 | A2 * | 10/1999 |
| EP | 1031322 | A2 * | 8/2000 |
| JP | 2000254133 | A * | 9/2000 |

* cited by examiner

HANDLE WITH REMOVABLE DISPOSABLE SURGICAL BLADE

BACKGROUND OF THE INVENTION

The present invention relates to a handle with removable disposable surgical blade and blade removal system including disposal container. The present invention constitutes a significant improvement over Applicant's prior invention as disclosed and claimed in U.S. Pat. No. 6,500,187, issued Dec. 31, 2002. The disclosure of Applicant's prior patent is incorporated by reference herein along with all of the prior art cited during the prosecution thereof.

Applicant's prior invention constituted an effective and useful surgical saw blade system including a scalpel detachably mountable to an elongated handle and with the scalpel easily disposable. However, several minor deficiencies in Applicant's prior invention combined together to lead Applicant to the conclusion that improvements could be made to create an easier to use, simpler and more effective blade-handle system. In Applicant's prior invention, the scalpel blade has a fitting with a proximal opening that receives the distal end of the handle. In that system, exacting tolerances in the tapers of the recess in the fitting and the protrusion on the distal end of the handle created manufacturing difficulties. In order to obtain a precise fit between the handle and blade, tolerances had to be maintained within 0.001 to 0.002 inches. Applicant found that manufacturers were unable to maintain such tolerances, thereby resulting in slight wobbling between the blade and handle. In the surgical setting, wobbling is impermissible.

An additional concern arose in that there were circumstances during which the blade could inadvertently detach from the handle or loosen from it during use. Such a possibility is intolerable in the surgical setting and, as such, a need arose to improve upon the blade-handle system to absolutely preclude such a possibility.

In addition, in the prior system, when the surgeon decided to remove the blade from the handle and replace it with a fresh blade, the technique used by the surgeon was to grip the sides of the fitting and pull the blade off the handle. This technique introduced danger to the surgeon since his or her fingers would be quite close to the actual blade edge, thereby creating the possibility of puncture or cutting of the surgeon's fingers, though inadvertently. Thus, Applicant's experience with the prior system led to the conclusion that a disposal system would have to be devised that would permit the surgeon to remove the blade from the handle while gripping the handle and keeping his or her hands and fingers far away from the blade itself. It is with these thoughts and concerns in mind that the present invention was developed.

SUMMARY OF THE INVENTION

The present invention relates to a handle with removable disposable surgical blade and blade removal system including disposal container. The present invention includes the following interrelated objects, aspects and features:

(1) In a first aspect of the present invention, a handle is provided that includes a distal end with a recess sized to receive the proximal end of a blade assembly. As will be better understood in conjunction with description of the blade assembly, the recess includes a proximal notch as well as opposed inwardly facing distal ridges obliquely angled with respect to the axis of elongation of the handle and designed to engage grooves in the blade assembly to assist in maintaining the blade assembly and handle in assembled relation.

(2) The blade assembly includes a blade portion having a distal cutting edge and a proximal portion embedded in a fitting having a proximally directed protrusion sized and configured to be received within the handle notch to permit releasable locking of the blade assembly within the recess in the handle. The notch and protrusion have arcuate surfaces permitting the protrusion to pivot within the notch when the blade assembly is being coupled or uncoupled with respect to the handle. In the preferred embodiment of the present invention, the fitting is made of a plastic material and is molded about the proximal end of the blade portion.

(3) The fitting also includes side faces having opposed grooves obliquely disposed so that they are engaged by the distal ridges within the handle recess to assist in locking the blade assembly to the handle. The fitting also includes an upwardly and proximally extending catch that engages a distal surface on the handle to assist in locking the blade assembly to the handle.

(4) In a further aspect, the recess of the handle includes lateral inner surfaces that are tapered, converging toward one another from the lower opening of the recess toward an upper termination of the recess. The side faces of the blade fitting are tapered to the same degree so that as the fitting is pushed upwardly within the handle recess, the side faces of the fitting engage the lateral inner surfaces of the recess to provide an interference fit therebetween. The degree of taper of the lateral inner surfaces of the recess and the side faces of the fitting may be in the range of about 3° within a tolerance of 0.003-0.004 of an inch.

(5) An integral part of the present invention consists of the blade removal system that permits the blade assembly to be easily and effectively removed from the handle without any danger of cutting or puncturing the fingers or hands of the surgeon. The blade removal system includes a container having a removable lid, with the lid having a centrally located, generally rectangular opening therein leading to a short passageway sized and configured to receive the blade assembly therein. The blade assembly may be inserted into the recess until the fitting engages within a rectangular opening therein. In that orientation, the handle may be pivoted to unlock the blade assembly from the handle, whereupon the blade assembly falls through the opening and into the container. In the preferred embodiment of the present invention, the container is made of a transparent plastic material permitting easy viewing of the blade assembly as removed from the handle and located therein.

As such, it is a first object of the present invention to provide a handle with removable disposable surgical blade and blade removal system including disposal container.

It is a further object of the present invention to provide such a handle and blade assembly in which the blade assembly includes a blade portion with a fitting molded about the proximal end thereof.

It is a still further object of the present invention to provide such an invention wherein the handle includes a distally disposed recess sized and configured to removably receive the fitting of the blade assembly.

It is a still further object of the present invention to provide such an invention in which four distinct locking mechanisms between the handle and the blade assembly are provided.

It is a yet further object of the present invention to provide a blade removal system in which the blade assembly may easily be removed from the handle without danger to the surgeon.

It is a still further object of the present invention to provide such a blade removal system in which the blade assembly may be inserted into an opening in the lid of a disposal container and the handle may be pivoted to easily unlock the blade assembly from the handle, resulting in the blade assembly falling into the interior of the container.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 1:
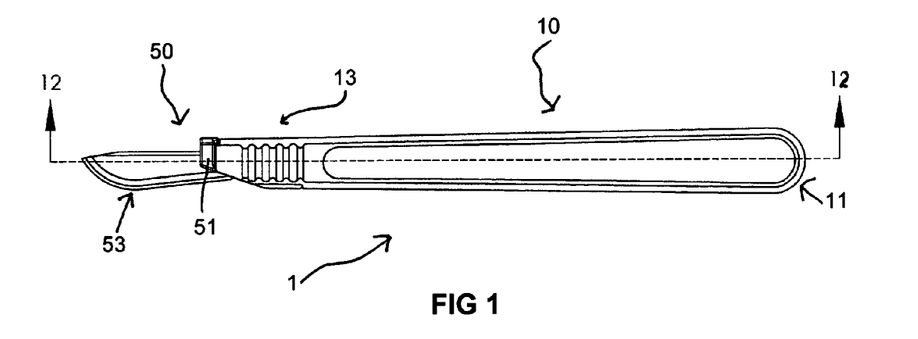
FIG. 1 shows a side view of the handle and blade assembly of the present invention as assembled.
Figure 2:
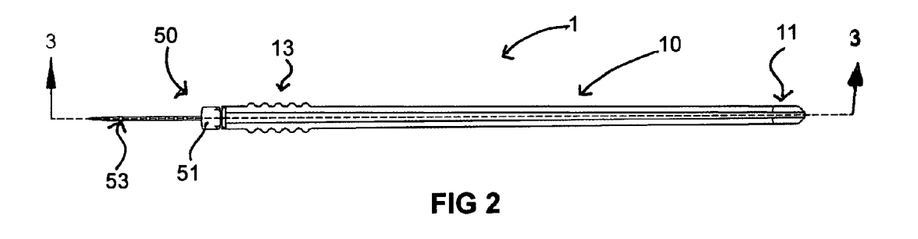
FIG. 2 shows a top view of the assembly of FIG. 1.

With reference, first, to FIG. 1, the present invention is generally designated by the reference numeral 1 and is seen to include a handle 10 and a blade assembly 50. The handle 10 includes a proximal end 11 and a distal end 13. The blade assembly includes a proximally located fitting 51 and a distal blade portion 53. Many of these features are also seen in FIG. 2.

Figure 3:
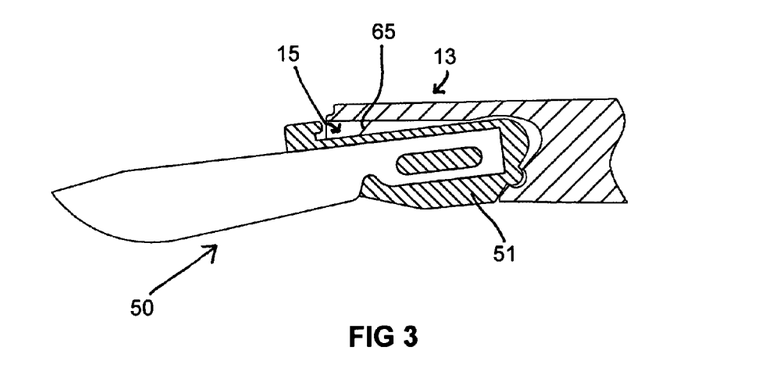
FIG. 3 shows a cross-sectional view along the line 3-3 of FIG. 2.
Figure 4:
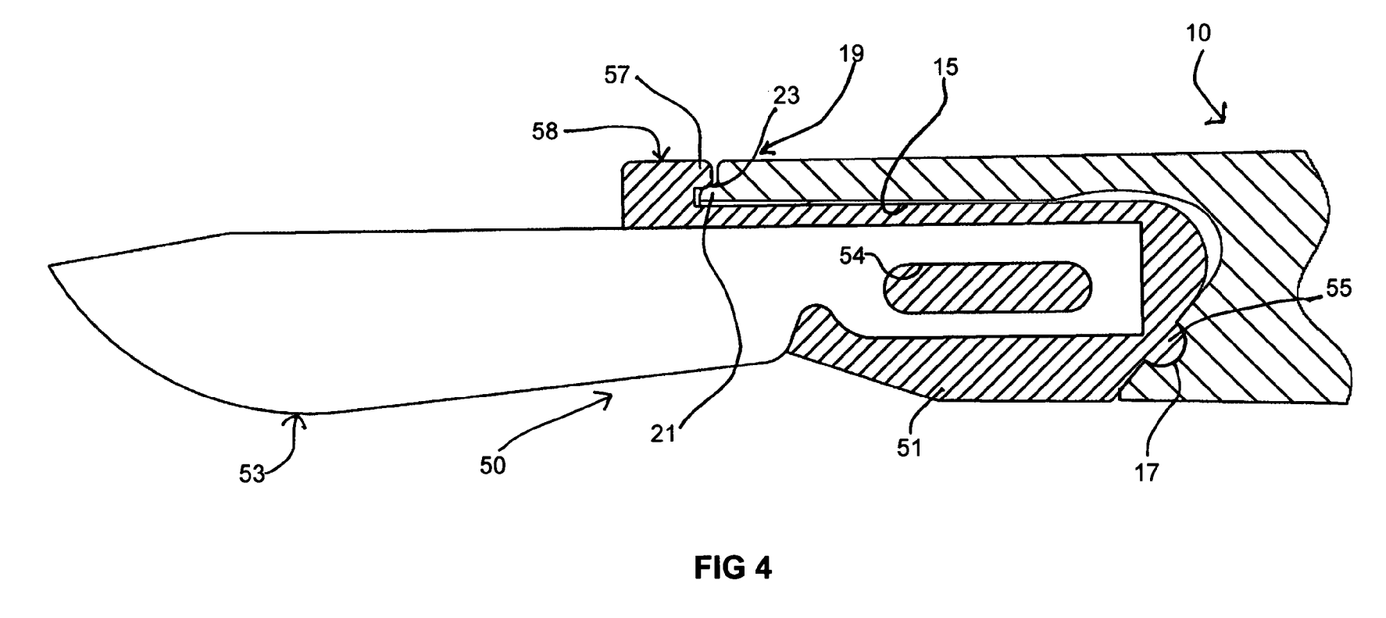
FIG. 4 shows a cross-section of the blade assembly and the distal portion of the handle enlarged and with the blade assembly in locked position.
Figure 5:
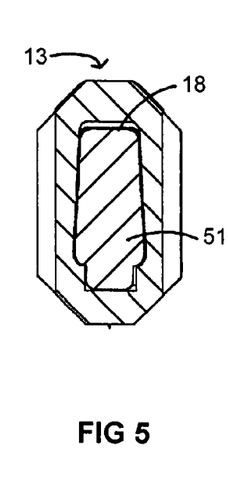
FIG. 5 shows a cross-sectional view along the line 5-5 of FIG. 10.
Figure 6:
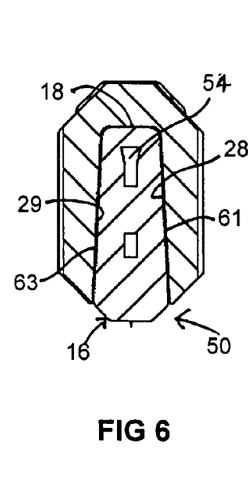
FIG. 6 shows a cross-sectional view along the line 6-6 of FIG. 10.
Figure 7:
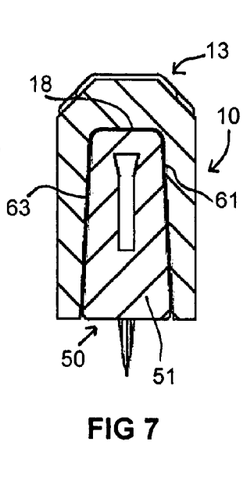
FIG. 7 shows a cross-sectional view along the line 7-7 of FIG. 10.

With reference to FIG. 3, the distal end 13 of the handle 10 includes a recess 15 sized and configured to receive the fitting 51 releasably fixed therein. With reference to FIG. 4, it is seen that the recess 15 includes a proximal notch 17 sized to receive a protrusion 55 at the proximal end of the fitting 51. Also seen in FIG. 4 is a distal surface 19 on the handle 10 that includes a distally directed tang 21 as well as a shoulder 23. The fitting 51 includes a distally directed catch 57 that engages over the tang 21 and into the shoulder 23 to assist in locking the blade assembly 50 into the recess 15 of the handle 10.

Figure 12:
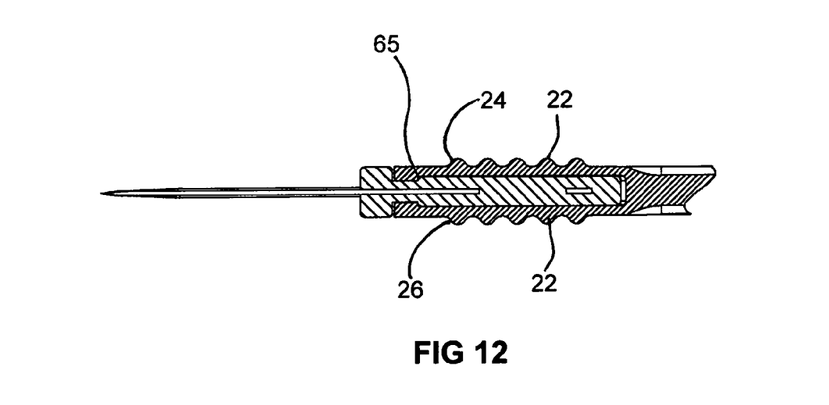
FIG. 12 shows a cross-sectional view along the line 12-12 of FIG. 1.

As also seen in FIG. 4, the fitting 51 is preferably molded over the proximal end of the blade portion 53. For this purpose, the blade portion 53 includes a proximal opening 54. Thus, when the fitting 51 is molded thereover, plastic enters the opening 54 to assist in locking the fitting 51 and blade portion 53 together in fixed relation. The distal handle 13 has opposed sets of ribs 22 (FIG. 12) designed to be gripped by the surgeon's fingers. As seen in FIG. 12, the most distal ribs 22 have distal surfaces 24 and 26, respectively, for a purpose to be described in more detail hereinafter.

Figure 11:
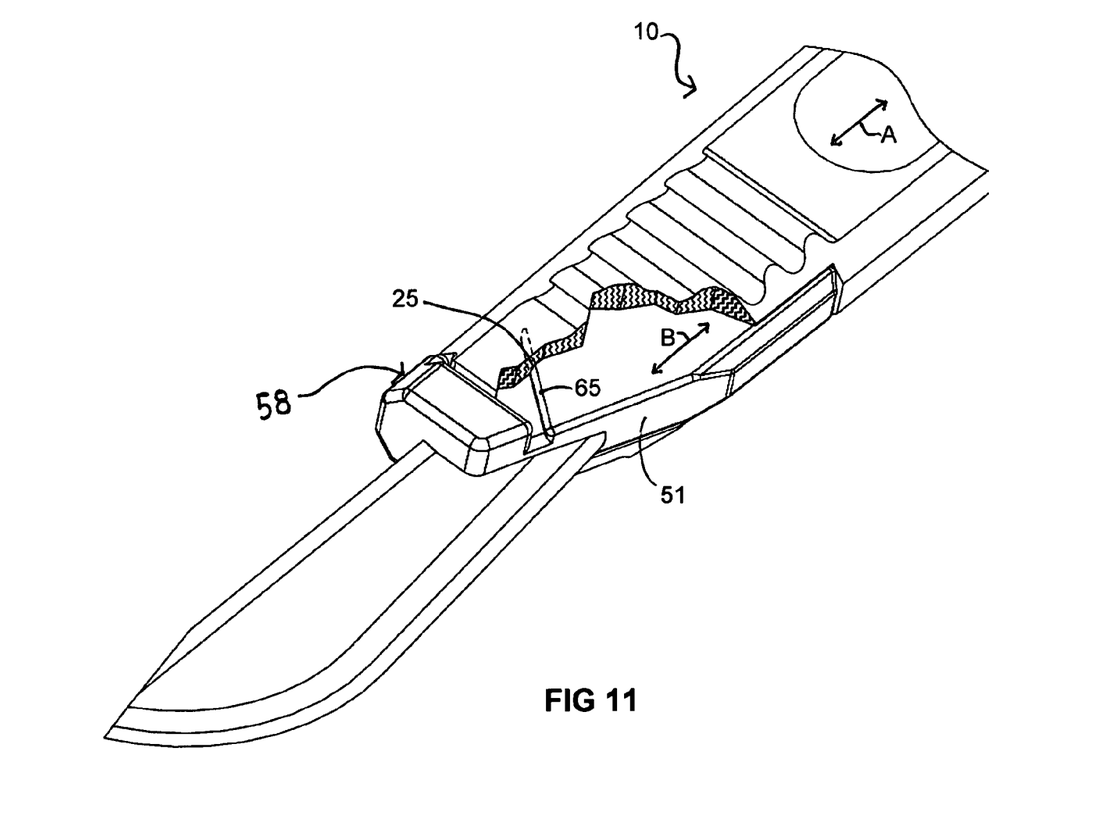
FIG. 11 shows a perspective view of the blade assembly and the distal portion of the handle as assembled with portions broken away to show detail.

With reference to FIGS. 10-13, a further feature assists in locking the blade assembly 50 within the recess 15 of the handle 10. In this regard, first, with reference to FIG. 13, the fitting 51 includes opposed side surfaces 61 and 63. These surfaces, near the distal end of the fitting 51, include a pair of opposed ridges 65 and 67. As best seen in FIG. 11, with reference to the ridge 65, the ridges are oriented at an oblique angle with respect to the axis of elongation B of the fitting 51 and with respect to the axis of elongation A of the handle 10. Both axes are schematically depicted in FIG. 11.

Figure 13:
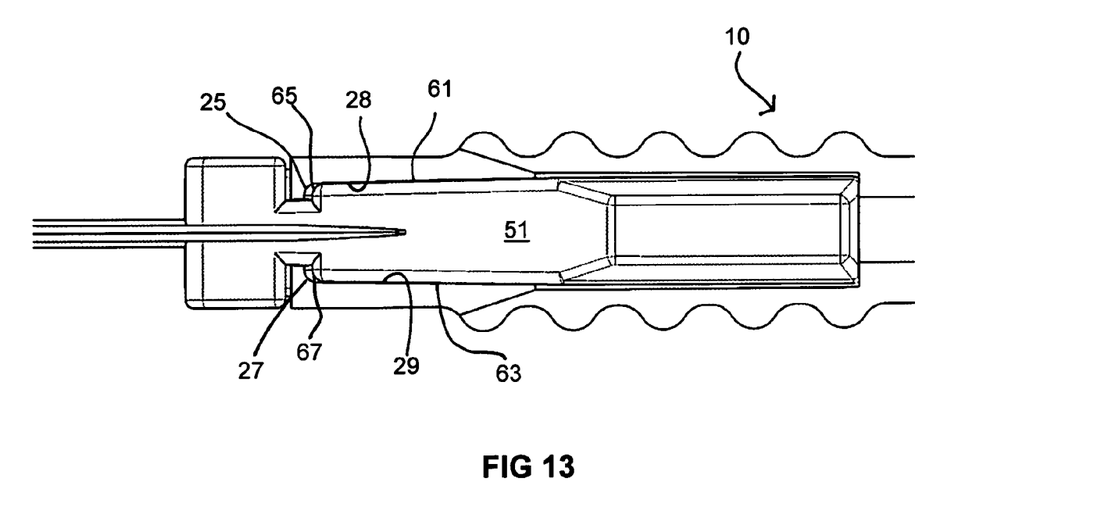
FIG. 13 shows a bottom view of the distal handle and blade fitting.

With further reference to FIGS. 11-13, it is seen that the recess 15 of the handle 10 is in part defined by inner surfaces 28 and 29. Near the distal end of the handle 10, those side surfaces 28 and 29 curve toward one another as shown by the reference numerals 25 and 27, respectively. The curved surfaces 25 and 27 in the recess 15 overlie the ridges 65 and 67 on fitting 51 when the blade assembly 10 is inserted within the recess 15 of the handle 10 to assist in holding the assembly together and to assist in precluding inadvertent and undesired removal of the blade assembly 50 from the handle 10. FIG. 11 shows the curved handle surface 25 that has the same oblique angle as that of the fitting ridge 65. The same is true of the ridge 67 and the surface 27 which are symmetrical with the ridge 65 and surface 25, respectively.

Figure 8:
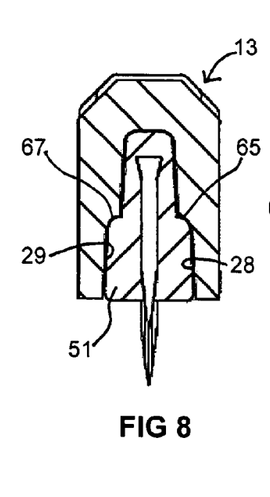
FIG. 8 shows a cross-sectional view along the line 8-8 of FIG. 10.
Figure 9:
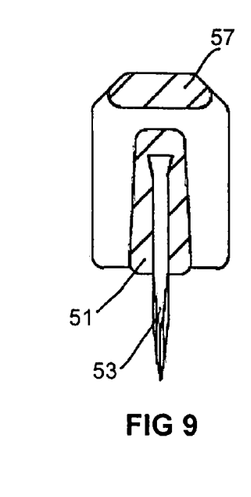
FIG. 9 shows a cross-sectional view along the line 9-9 of FIG. 10.
Figure 10:
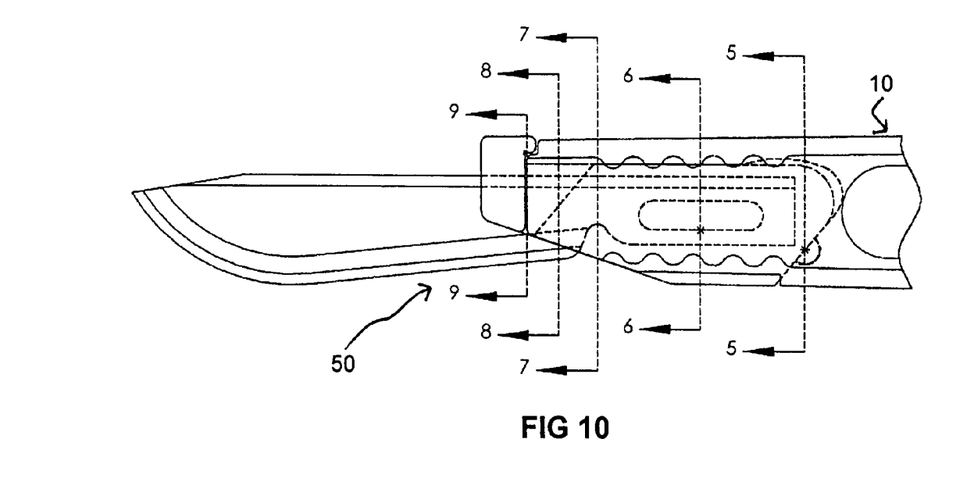
FIG. 10 shows a side view of the blade assembly and the distal portion of the handle and with certain structural features shown in phantom.

FIGS. 5-9 are cross-sections showing the assembled relation between the blade assembly 50 and the handle 10. As clearly understood from FIGS. 5-9, the handle recess 15 has a lower opening 16 and the lateral inner surfaces 28 and 29 of the recess 15 are tapered in a direction toward convergence in the upward direction toward the upper wall 18 of the recess 15. Similarly, the opposed outer walls 61 and 63 of the blade assembly 50 are tapered toward one another at the same taper as that of the surfaces 28 and 29. In the preferred embodiment of the present invention, the taper is about 3° to within a tolerance of 0.003 to 0.004 of an inch. Thus, as the fitting 51 of the blade assembly 50 is pushed upwardly in the view of FIGS. 5-9 into the recess 15, an interference fit develops that enhances retention of the blade assembly 50 within the recess 15. FIG. 8 shows the interrelationship between the ridges 65, 67 of the fitting 51 and the inner surfaces 28, 29 of the distal handle 13 recess 15.

Figure 14:
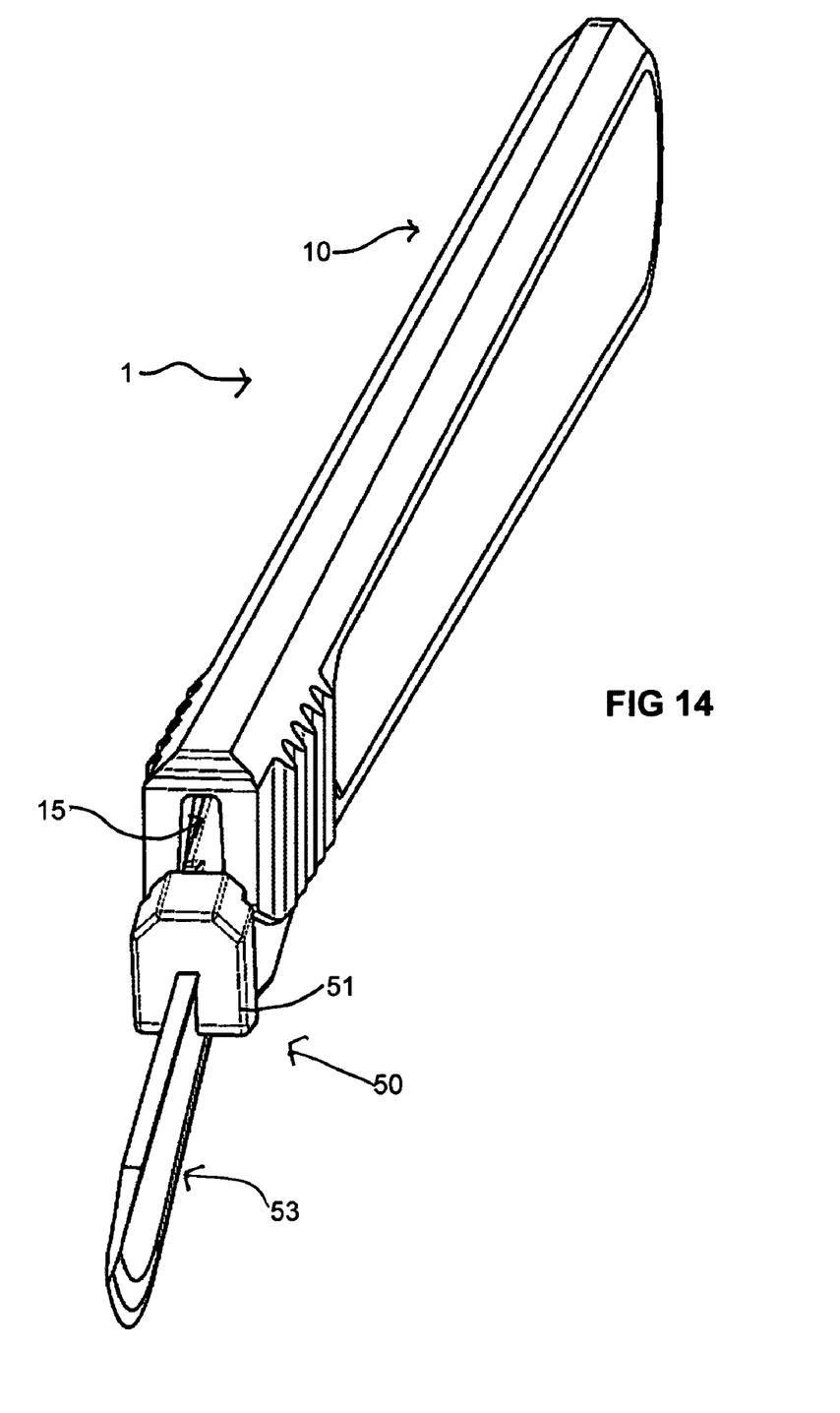
FIG. 14 shows a front perspective view of the handle and blade assembly with the blade assembly partially removed from the handle.

Thus, in releasably assembling the blade assembly 50 to the handle 10, reference is first made to FIG. 4. In this regard, when assembling the blade assembly 50 to the handle 10, the protrusion 55 at the proximal end of the fitting 51 is inserted within the handle notch 17 within the recess 15 of the handle 10. Thereafter, with the blade assembly 50 in an orientation such as shown in FIGS. 3 and 14, the blade assembly 50 is pivoted in the clockwise direction in the view of FIG. 3 with the curved surfaces of the protrusion and notch facilitating this movement and ensuring that the fitting 51 of the blade assembly 50 seats all the way into the handle recess 15. As this pivoting takes place, the interference fit caused by the tapers of the walls 61 and 63 of the fitting 51 and the surfaces 28 and 29 of the recess 15 tightens the blade assembly 50 fitting 51 within the recess 15. Further movement causes engagement between the ridges 65, 67 and the handle surfaces 25 and 27. Just as complete engagement between the ridges and surfaces occurs, with reference to FIG. 4, the fitting catch 57 overlies the inner handle surface 21 and provides the final lock to lock the blade assembly 50 to the handle 10. In that orientation of parts, the surgeon may utilize the device 1 in performing surgical cuts.

Figure 15:
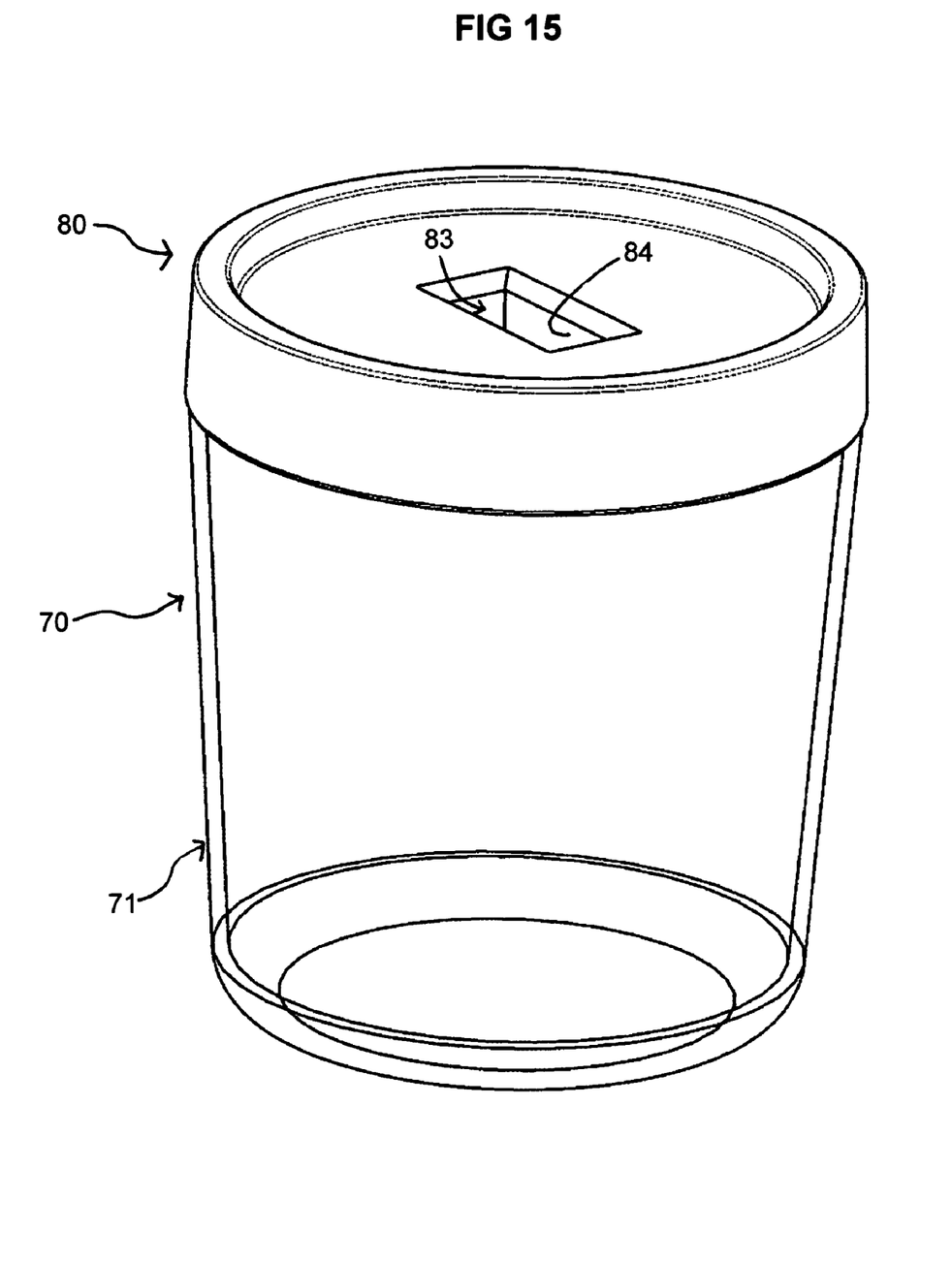
FIG. 15 shows a perspective view of a disposal container.
Figure 16:
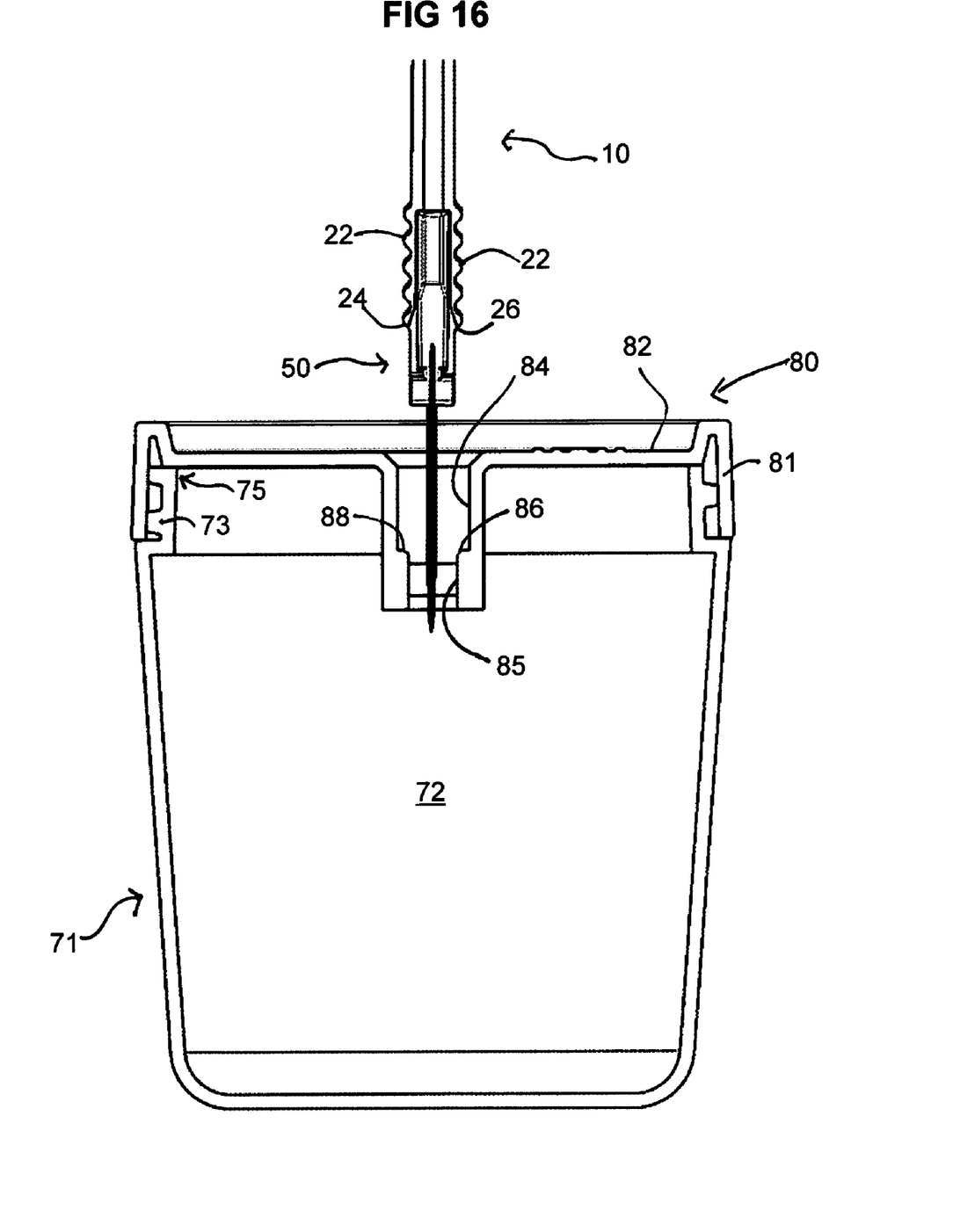
FIG. 16 shows a side view partially in cross-section of the disposal container of FIG. 14 including a handle and blade assembly with the blade assembly partially inserted within an opening in the cover of the disposal container.
Figure 17:
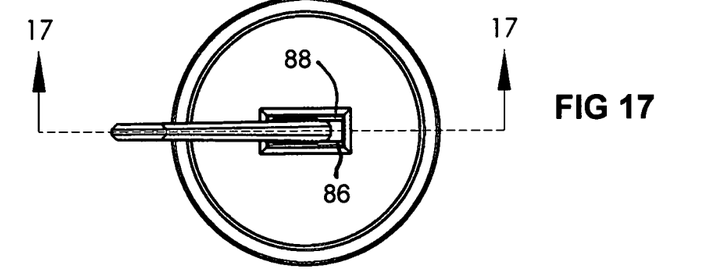
FIG. 17 shows a top view of the disposal container with the distal end of the handle and blade assembly inserted within the passageway thereof.

With reference now to FIGS. 15-19, a blade removal system forms an integral part of the present invention. The design features of the handle 10 and blade assembly 50 were dictated, in part, by the design of the removal system. Reference is first made to FIGS. 15 and 16 which show a disposal container 70 including a container 71 that, in the preferred embodiment, may be transparent, and a container cover 80. With further reference to FIGS. 15 and 16, the cover 80 includes a central rectangular opening 83 that defines a passageway 84, also seen in FIG. 15 in more detail. The container 71, with reference to FIG. 16, includes an upper portion 73 comprising screw threads and an opening 75 that is covered by the cover 80. The cover 80 includes a peripheral downwardly depending lip 81 that overlies the threaded portion 73 of the container 71 to removably install the cover 80 thereon. The container 71 defines an internal chamber 72.

The passageway 84 extends downwardly from the upper surface 82 of the cover 80 and includes a narrowed lower section 85 that is sized to allow the blade assembly 50 to completely pass therethrough. Opposed linear shoulders 86 and 88 (FIGS. 16 and 17) define the uppermost extent of the portion 85 and are dimensioned to engage the surfaces 24, 26 of the distal ribs 22 of the handle 10 to prevent travel of the handle 10 into the portion 85.

Figure 18:
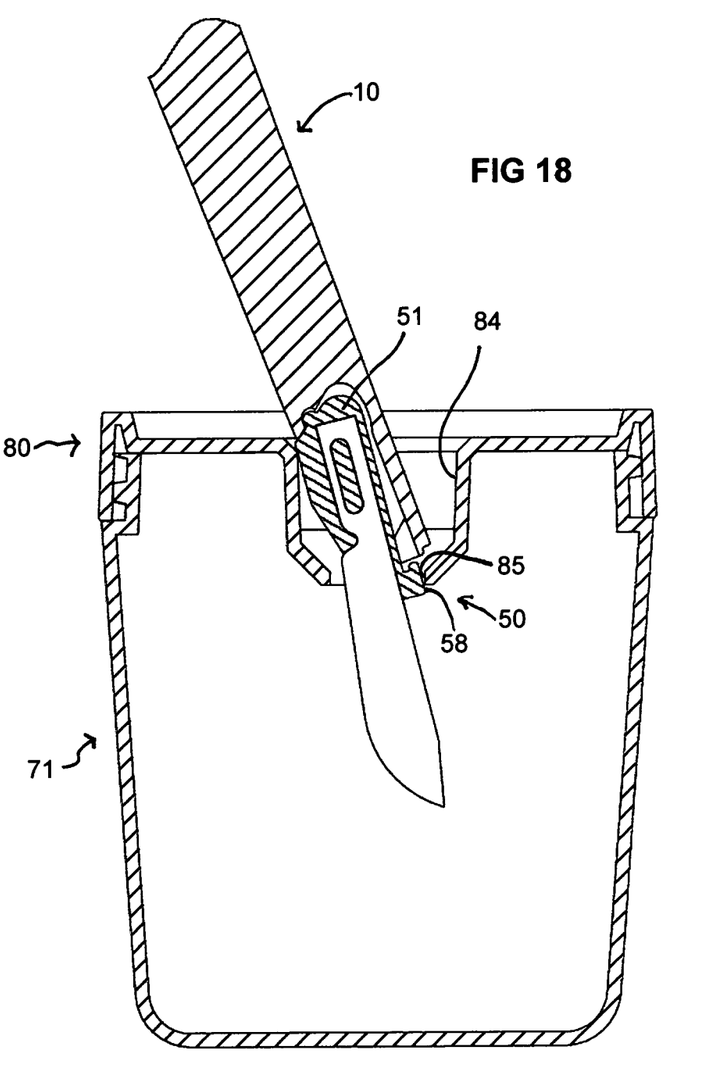
FIG. 18 shows a cross-sectional view along the line 17-17 of FIG. 16 through the disposal container as well as through a handle and blade assembly showing the commencement of the process of removing the blade assembly from the handle.
Figure 19:
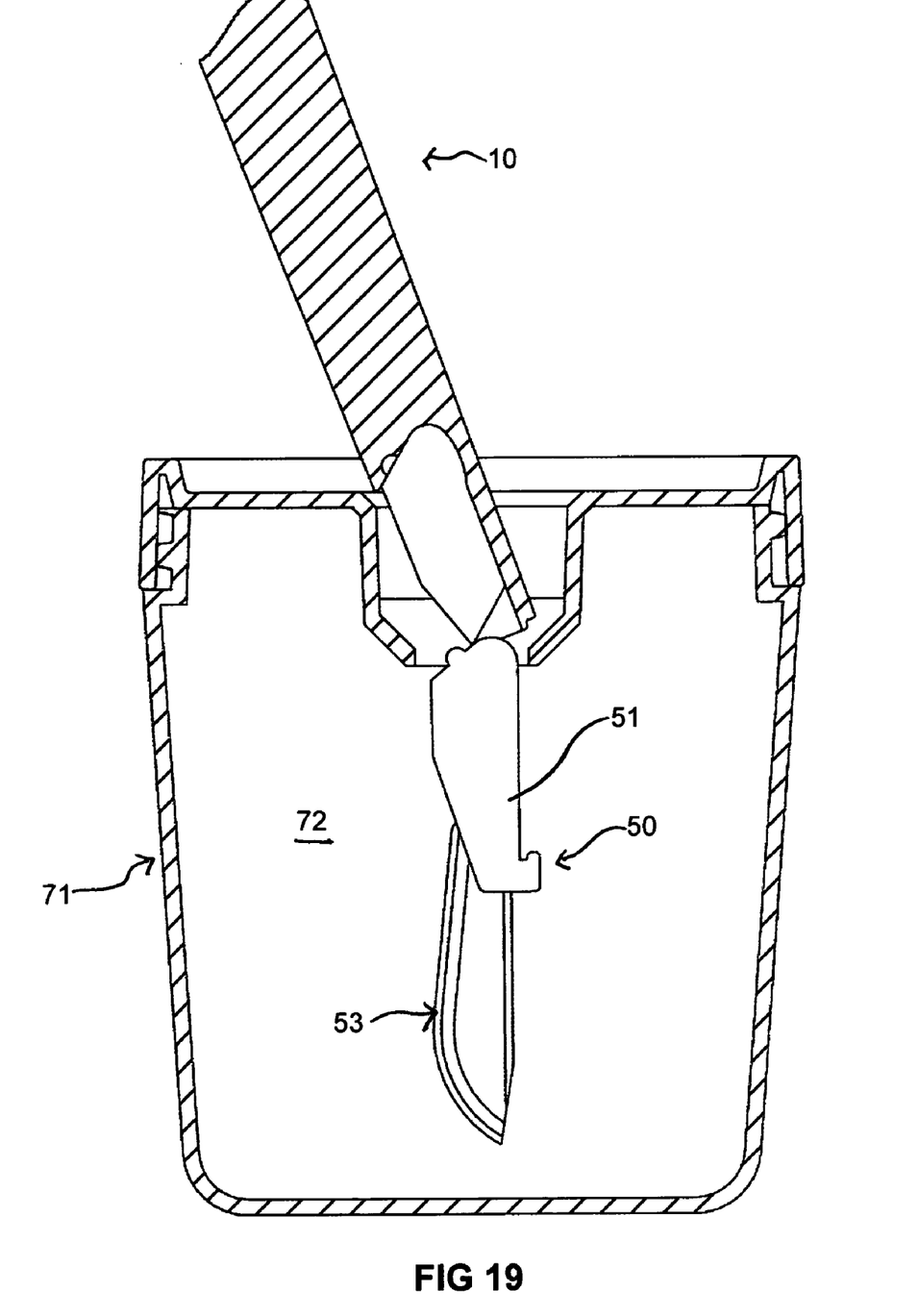
FIG. 19 shows a view similar to that of FIG. 18, but showing completion of the removal process.

With reference to FIG. 18, it is seen that as the fitting 51 of the blade assembly 50 has its surface 58 (FIG. 4) engaging the narrowed portion or buttress 85 of the passageway 84, the surfaces 24, 26 of the distal ribs 22 of the handle 10 engage the shoulders 86, 88 preventing further downward movement of the handle 10, in the view of FIG. 18. Thereafter, the handle 10 may be pivoted in the counterclockwise direction in the view of FIG. 18 to dislodge the catch 57 from the shoulder 23 and the inner surface 21 to thereby begin the process of detaching the blade assembly 50 from the handle 10. With reference to FIG. 19, further pivoting movement of the handle 10 in the same direction as described above with respect to FIG. 18 completely detaches the handle 10 and the blade assembly 50 without damage to either component and the blade assembly 50 may fall through the force of gravity into the chamber 72 within the container 71. In this way, the blade assembly 50 may be removed from the handle 10 without any need for the surgeon or any other medical personnel to actually have to grasp the fitting 51 near the blade portion 53. In this way, medical safety is enhanced and spread of disease via the contaminated blade portion 53 is absolutely precluded.

As such, an invention has been disclosed in terms of a preferred embodiment thereof which fulfills each and every one of the objects of the invention as set forth above, and provides a new and useful handle with removable disposable surgical blade and blade removal system including disposal container of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:

1. A surgical scalpel comprising:
   a) a handle having a proximal end and a distal end;
   b) the distal end defining a recess including an arcuate notch opening distally, and said recess having lateral opposed flat side surfaces converging from a lower opening of said recess toward an upper termination of said side surfaces, said upper termination comprising a horizontal flat surface;
   c) a blade assembly including a blade portion having a proximal end embedded within a plastic molded fitting, the fitting having an arcuate protrusion extending proximally and receivable within said notch, and flat side walls converging in correspondence to said side surfaces, said side walls terminating at a horizontal flat wall;
   d) said blade assembly being coupled to said handle with said protrusion received with said notch, with said side walls engaging said side surfaces in a frictional interference fit, and with said horizontal flat surface engaging said horizontal flat wall.

2. The scalpel of claim 1, wherein said handle includes a distal lip, said fitting including a catch that overlies said lip when said blade assembly is coupled to said handle.

3. The scalpel of claim 2, wherein said fitting includes opposed ridges extending laterally therefrom, said recess including opposed ridge engaging surfaces that engage said ridges when said blade assembly is coupled to said handle.

4. The scalpel of claim 3, wherein said handle has an axis of elongation, said ridge engaging surfaces extending obliquely with respect to said axis.

5. The scalpel of claim 3, wherein said fitting has an axis of elongation, said ridges extending obliquely with respect to said axis.

6. The scalpel of claim 5, wherein said arcuate notch and protrusion allow said fitting to pivot about said notch forcing full seating of the fitting in said handle recess during attachment to said handle.

7. The scalpel of claim 1, wherein said fitting includes opposed ridges extending laterally therefrom, said recess including opposed ridge engaging surfaces that engage said ridges when said blade assembly is coupled to said handle.

8. The scalpel of claim 1, wherein said opposed side surfaces of said recess converge at an angle of about 3°.

9. The scalpel of claim 8, wherein said side walls of said fitting converge at an angle of about 3°.

10. The scalpel of claim 1, wherein said arcuate notch and protrusion allow said fitting to pivot about said notch during attachment to said handle.

11. A surgical scalpel comprising:
   a) a handle having a proximal end and a distal end;
   b) the distal end defining a recess including an arcuate notch opening distally and lateral opposed flat side surfaces converging from a lower opening of said recess toward an upper termination of said side surfaces, said upper termination comprising a horizontal flat surface;
   c) a blade assembly including a blade portion having a proximal end embedded within a molded fitting, the fitting having an arcuate protrusion extending proximally and receivable within said notch, and flat side walls converging in correspondence to said side surfaces, said side walls terminating at a horizontal flat wall;

d) said blade assembly being coupled to said handle with said protrusion received with said notch, with said side walls engaging said side surfaces in a frictional interference fit, and with said horizontal flat surface engaging said horizontal flat wall;

e) said handle including a distal lip, said fitting including a catch that overlies said lip when said blade assembly is coupled to said handle, said fitting further including opposed ridges extending laterally therefrom, said recess including opposed ridge engaging surfaces that engage said ridges when said blade assembly is coupled to said handle.

12. The scalpel of claim 11, wherein said fitting has an axis of elongation, said ridges extending obliquely with respect to said fitting axis, said handle having an axis of elongation, said ridge engaging surfaces extending obliquely with respect to said handle axis.

13. The scalpel of claim 11, wherein said fitting is made of plastic molded over said blade portion.

14. The scalpel of claim 11, wherein said opposed side surfaces of said recess converge at an angle of about 3° and said side walls of said fitting converge at an angle of about 3°.

15. The scalpel of claim 11, wherein arcuate notch and protrusion permit said fitting to pivot about said notch during attachment to said handle.

* * * * *